United States Patent
Franzrahe et al.

(10) Patent No.: US 11,958,793 B2
(45) Date of Patent: Apr. 16, 2024

(54) UREA PRODUCTION PLANT AND SCRUBBING SYSTEM

(71) Applicants: THYSSENKRUPP FERTILIZER TECHNOLOGY GMBH, Dortmund (DE); thyssenkrupp AG, Essen (DE)

(72) Inventors: Harald Franzrahe, Dortmund (DE); Axel Erben, Dortmund (DE); Simon Koch, Dortmund (DE)

(73) Assignees: THYSSENKRUPP FERTILIZER TECHNOLOGY GMBH, Dortmund (DE); thyssenkrupp AG, Essen (DE)

( * ) Notice: Subject to any disclaimer, the term of this patent is extended or adjusted under 35 U.S.C. 154(b) by 845 days.

(21) Appl. No.: 16/982,165

(22) PCT Filed: Apr. 12, 2019

(86) PCT No.: PCT/EP2019/059485
§ 371 (c)(1),
(2) Date: Sep. 18, 2020

(87) PCT Pub. No.: WO2019/206684
PCT Pub. Date: Oct. 31, 2019

(65) Prior Publication Data
US 2021/0024460 A1 Jan. 28, 2021

(30) Foreign Application Priority Data
Apr. 23, 2018 (EP) .................................... 18168762

(51) Int. Cl.
*C07C 273/16* (2006.01)
*B01D 5/00* (2006.01)
(Continued)

(52) U.S. Cl.
CPC ............ *C07C 273/16* (2013.01); *B01D 5/006* (2013.01); *B01D 9/0027* (2013.01); *B01D 47/06* (2013.01);
(Continued)

(58) Field of Classification Search
None
See application file for complete search history.

(56) References Cited

U.S. PATENT DOCUMENTS 4,219,589 A  8/1980  Goethals
1,330,319 A  5/1982  Bexton
(Continued)

FOREIGN PATENT DOCUMENTS

DE    3116778 A    2/1982
EP    2 192 099 A1    6/2010
(Continued)

OTHER PUBLICATIONS

International Search Report issued in PCT/EP2019/059485, dated Jun. 26, 2019.
(Continued)

*Primary Examiner* — Amy C Bonaparte
(74) *Attorney, Agent, or Firm* — thyssenkrupp North America, LLC

(57) ABSTRACT

A urea production plant including a synthesis and recovery section has a first evaporation section connected with the synthesis and recovery section and a first condensation section. A granulation section is connected to the first evaporation section. A scrubbing section is connected to the granulation section. A second evaporation section is connected to the scrubbing section. The second evaporation section is connected to the granulation section. A second condensation section is connected to the second evaporation section. A quenching section includes a liquid inlet for the
(Continued)

distribution of a quenching liquid is located and connected between the granulation section and the scrubbing section and the quenching section is connected to a quenching liquid providing section and the second condensation section.

11 Claims, 3 Drawing Sheets

(51) Int. Cl.
*B01D 9/00* (2006.01)
*B01D 47/06* (2006.01)
*B01D 53/14* (2006.01)
*C05C 9/00* (2006.01)
*C05G 5/12* (2020.01)
*C07C 273/04* (2006.01)
*B01D 47/00* (2006.01)

(52) U.S. Cl.
CPC .......... *B01D 53/1456* (2013.01); *C05C 9/005* (2013.01); *C05G 5/12* (2020.02); *C07C 273/04* (2013.01); *B01D 2009/0086* (2013.01); *B01D 47/00* (2013.01)

(56) References Cited

U.S. PATENT DOCUMENTS

| | | |
|---|---|---|
| 4,701,353 A | 10/1987 | Mutsers |
| 8,466,315 B2 | 6/2013 | Niehues et al. |
| 9,732,033 B2 | 8/2017 | Mennen et al. |
| 2016/0184758 A1 | 6/2016 | Soons |
| 2016/0303502 A1 | 10/2016 | Higgins |
| 2017/0320816 A1 | 11/2017 | Higgins |

FOREIGN PATENT DOCUMENTS

| | | |
|---|---|---|
| JP | 2012-509833 A | 4/2012 |
| JP | 2015-520741 A | 7/2015 |
| NL | 2009295 C | 2/2014 |
| WO | 2005032696 A | 4/2005 |
| WO | 2010/060535 A | 6/2010 |
| WO | 2013165245 A | 11/2013 |
| WO | 2014094987 A | 6/2014 |
| WO | 2015/002535 A | 1/2015 |
| WO | 2015072854 A | 5/2015 |
| WO | 2016/099267 A | 6/2016 |
| WO | 2017/196167 A1 | 11/2017 |

OTHER PUBLICATIONS

Jozef H. Messen, Ullmann's Encyclopedia of Industrial Chemistry, 2010, Urea, chapter 4 [DOI: 10.1002/14356007.a27_333.pub2].

UREA PRODUCTION PLANT AND SCRUBBING SYSTEM

CROSS REFERENCE TO RELATED APPLICATIONS

This application is a U.S. National Stage Entry of International Patent Application Serial Number PCT/EP2019/059485, filed Apr. 12, 2019, which claims priority to European Patent Application No. EP 18168762.5, filed Apr. 23, 2018, the entire contents of both of which are incorporated herein by reference.

FIELD

The present disclosure generally relates to a urea production plant, scrubbing, and quenching.

BACKGROUND

Due to a continuous world population growth, there is an ongoing need in providing reliable, easy producible and cheap fertilizers. These conventional fertilizers may contain nitrogen, phosphate, sulfur, potassium or micronutrients.

A common, widely used fertilizer contains urea as its main component. The water soluble urea rapidly decomposes in the soil, providing ammonia and nitrate compounds. Based on the application, the fertilizer may contain only urea or a combination of urea with one or more of the before mentioned components, e.g. phosphate, sulfur, potassium or micronutrients.

Urea can be produced on a large industrial scale by reacting ammonia with carbon dioxide via a (simplified) two-step reaction:

$$2NH_3 + CO_2 \rightleftharpoons H_2N\text{---}COONH_4 \qquad [1]$$

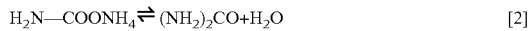

$$H_2N\text{---}COONH_4 \rightleftharpoons (NH_2)_2CO + H_2O \qquad [2]$$

The absorbance of water based on the hygroscopic nature of urea easily results in uncontrolled aggregation, quality degradation and caking of fine, untreated urea particles. This process can negatively affect the solubility, bulk storage, durability or chemical stability of the urea fertilizer. In addition, the uncontrolled gain in weight by absorbing water increases the transport weight and costs. Therefore, further post synthesis process steps are necessary in order to provide a transportable and storable urea fertilizer. Common technical processes include diverse granulation technics like prilling, drum granulation or fluid-bed granulation. Especially prilling processes suffer from some critical drawbacks like relatively soft particles and sometimes deformed inhomogeneous particles.

These problems can be avoided by using a fluid-bed granulation process, which results in harder, more stable and homogeneous granules. The resulting granular urea is particularly suitable for bulk blending operations. Furthermore, there is reduced segregation or mechanical damage during mixing and transporting of the urea based fertilizer.

Examples of fluid-bed granulation process of urea can be found in WO 2010/060535 A1, e.g. in paragraphs [0025]-[0035], FIG. 1 or in U.S. Pat. No. 4,701,353 A, DE 31 16 778 A1 and U.S. Pat. No. 4,219,589 A.

Urea fertilizers can be combined with ammonia sulfate or elemental sulfur, therefore providing both plant nutrients in one fertilizer. Ammonia sulfat can be directly used by the plant, whereas elemental sulfur needs to be decomposed by soil microorganisms, thereby providing long-term plant nutrients. Examples of urea/sulfur granules can be found e.g. in U.S. Pat. No. 4,330,319 A.

The fluid-bed granulation process is based on providing granulation seeds, which grow by accretion of very small droplets of a growth liquid. These small droplets can be provided via an "atomized" liquid urea melt. The term "atomized" used in the description refers to a mixing process of the liquid urea melt (or other suitable fertilizer melts) with a pressuring pressurized medium like air. This mixing process creates a liquid/gas emulsion, dispersion or an aerosol of small droplets. The term "atomized" should therefore not be confused with a separating of molecular bonds on an atomic scale. Within the meaning of the invention, the term "melt" include salt melts and concentrated salt solution and mixtures thereof, preferably solutions containing more than 50 wt. % salt. The produced droplets may have a medium size distribution around 1 µm to 200 µm. These small melt droplets settle on the surface of the granulation seeds, thereby creating "growing" granulation particles. These fresh "in-situ" produced granules may commonly exhibit temperatures around 100° C. and are relatively soft. The particles are further cooled down in the fluid-bed of the granulator and/or in separate cooling compartments.

Due to the high heat of crystallization released during the granulation process, large amounts of cooling air are required to keep the preferable temperature range during granulation and subsequent cooling processes. This inevitably results in the release of significant amounts of dust into the cooling air. Due to environmental concerns, the resulting dust cannot be released to the surrounding atmosphere. Simultaneously, the removal of urea dust is difficult and challenging. Due to the general nature of the granulation process, the urea dust has to be removed from very large quantities of air. In addition the size of the particles may require different removal techniques. Established and well known procedures include wet scrubbing processes. Examples of suitable scrubbers can be found in WO 2005/032696 A1 (e.g. FIG. 1 and the corresponding description) or WO 2010/60535 A1. Further examples for the removal of very small particles are disclosed in WO 2014/094987 A1. An additional air pollutant is ammonia, which is inevitably released during the urea granulation process, too. Reliable ammonia removal processes include acid scrubbing, e.g. by contacting the ammonia laden air stream in an acid scrubber with sulfuric acid or nitric acid.

There is an ongoing need for further improvements in regard to the released dust and ammonia load of the granulation air in order to comply with emission control guidelines. In addition, even stricter environmental regulations are to be expected in the future.

Besides environmental concerns, the recycling of urea dust back to the granulation process gives further economic and financial benefits.

However, every additional process step will inevitably increase the energy and utility (e.g. water, steam and heat) consumption, thereby increasing the overall production costs.

WO 2015/072854 A1 discloses a method for the removal of soluble particulate matter from a gas stream, e.g. urea dust. The method comprises subjecting the off-gas to at least two quenching stages with an aqueous quenching liquid.

WO 2013/165245 A1 discloses a plant for the production of urea. The plant comprises conventional sections for synthesis and recovery, for evaporation and condensation, for urea finishing, and for dust scrubbing. According to the invention, an additional evaporation and condensation loop is introduced from and to the dust scrubbing section.

NL 2009295 C discloses a method for the production of granules, e.g. urea or ammonia nitrate. The disclosed method contains an arrangement of three scrubbers in order to reduce the submicron dust.

WO 2016/099267 A1 discloses a method for the removal of urea dust from the off-gas of a finishing section of a urea production plant. The method comprises subjecting the off-gas to quenching with water so as to produce quenched off-gas. The quenched off-gas is subjected to humidification by mixing said quenched gas stream with a humidification fluid selected from (a) saturated steam and (b) superheated steam mixed with a second aqueous stream, so as to produce a humidified gas stream, subjecting said humidified gas stream to particle separation.

US 2016/0184758 A1 discloses a method for the removal of urea dust from the off-gas of a finishing section of a urea production plant, the method comprises subjecting the off-gas to quenching with water so as to produce quenched off-gas, and subjecting the quenched off-gas to scrubbing using at least one venturi scrubber.

Thus, a need exists for a urea plant with a dust removal process with increased dust-removal efficiency and simultaneously decreasing process medium consumption.

DETAILED DESCRIPTION

Figure 1:
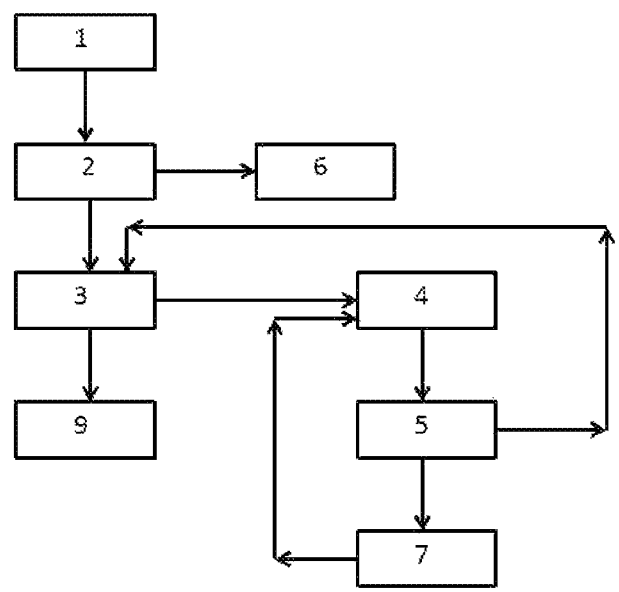
FIG. 1 is a schematic flow diagram of a plant setup/process for the preparation of urea granules.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The invention relates to a urea production plant with a new scrubbing and quenching setup, use of the inventive urea production plant for the production of urea fertilizer granules and a process for the preparation of urea granules.

In a further aspect it is another object of the present invention to provide the use of the urea plant for the production of fertilizer granules. The term "fertilizers granules" comprises particles, agglomerates and/or granules containing urea and further optional components.

The object of the present invention is also solved by a process for the preparation of urea granules according to claim 9. Preferred embodiments of the invention are subject to the corresponding dependent claims.

The urea production plant according to the invention comprises at least a synthesis and recovery section. In this synthesis and recovery section ammonia and urea are reacted to form urea. The principal and simplified schematic reactions are shown in equations [1] and [2]. The foregoing reaction leads to an aqueous urea solution after several synthesis and recovery steps. The principle synthesis and recovery steps are well known in the art, e.g. described in "Ullmann's Encyclopedia of Industrial Chemistry, 2010, Urea, chapter 4 [DOI: 10.1002/14356007.a27_333.pub2]". The resulting urea solution comprises typically around 50 wt. % to 80 wt. % of urea. A subsequent concentration step is necessary in order to achieve a urea solution with a water content typically below 5 wt. %. Preferably, the term urea solution comprises a solution containing 50 wt. % or more urea. Within the meaning of the invention, the term "urea solution" includes emulsions and/or dispersions and/or mixtures thereof containing at least 50 wt. % urea.

A first evaporation section is connected with the synthesis and recovery section and a first condensation section. The term "connected" within the meaning of the invention generally refers to connection means which are able/suitable to transport or transfer process liquids, solids or gases (or mixtures thereof), e.g. pipes, ducts, pumps, hoses and further includes tanks, reservoirs and/or pumps. This definition includes connection means suitable for low pressure gaseous and liquid mediums (below 1 bar) and high pressure (above 1 bar, preferably above 10 bar) gaseous and liquid mediums. The first evaporation section leads to a concentrated urea solution, preferably between 95 wt. % and 98 wt. % of urea and an aqueous vapor stream. Within the meaning of the invention, the term "connected" includes upstream and/or downstream process flow directions. Preferably, the first evaporation section transfers water containing vapor from the first evaporation section into a (mainly liquid), more preferably, reusable process liquid.

The concentrated urea solution can be transferred to a granulation section connected with the first evaporation section. The granulation section comprises fluid-bed, prilling, drum or other granulation sections, preferably a fluid-bed granulation section. Preferably the Fluid-bed granulator system comprises at least a fluid bed granulator with a granulator space inside the fluid-bed granulator. The fluid-bed granulator further comprises a perforated plate located inside the granulator space and spray nozzles located in, on or beside the perforated plate. A fluidization air inlet, preferably located below the perforated plate, provides the necessary fluidization air for the fluid bed of fertilizer granules. The term "fluidization air" includes air or inert gases like $CO_2$, nitrogen, argon or mixtures thereof. The spray nozzles are connected with supply lines for atomization air and supply lines for a concentrated urea solution. In addition, the fluid-bed granulator comprises a granulation seeds inlet. The term "a granulation seeds inlet" comprises internal and external devices, lines and openings for the introduction of granular seeds. The term "internal" refers to the production of granular seeds within the granulator. The term "external" refers to the providing provision or production of granular seeds from outside the granulator, e.g. via sieves or crushers outside the fluid-bed granulator. Furthermore the fluid-bed granulator comprises a granulator outlet opening and an air vent opening.

A scrubbing section is connected with the granulation section and a second evaporation section. The cooling air and off-gases from the granulation section are transferred to the scrubbing section. Preferably dust, e.g. urea dust, and/or chemical vapors like ammonia, which are created or released during the granulation process, are (at least partly) removed in the scrubbing unit. Due to the heat release of the granulation process, large amounts of cooling air are required to keep the preferable temperature range during granulation and subsequent cooling processes. This inevitably results in the release of significant amounts of dust and ammonia into the cooling air. Preferably, the scrubbing unit comprises at least a dust removing scrubber and an ammonia removing scrubber, more preferably an additional cooling scrubber for the fluid-bed cooler off-gases. Examples of suitable scrubbers can be found in WO 2005/032696 A1 (FIG. 1) or WO2010/60535 A1. An exemplary scrubbing setup includes (in the direction of the granulator off-gas flow): a dust scrubber, an acid scrubber and optionally a small particle (aerosol) scrubber, e.g. as disclosed in WO2014/094987 A1. Suitable scrubbing liquids include a dilute urea solution (e.g. between 5 wt. % and 60 wt. %) as a scrubbing liquid for the dust scrubber. Sulfuric acid, nitric acid and phosphoric acid solutions are suitable washing liquids for the acid scrubber. Ammonia is e.g. removed according to the exemplary equations [3] or [4]:

$$2NH_3 + H_2SO_4 \rightarrow (NH_4)_2SO_4 \quad [3]$$

$$NH_3 + HNO_3 \rightarrow NH_4NO_3 \quad [4]$$

The second evaporation section downstream of the scrubbing section is connected with the granulation section, allowing a reintroduction of the concentrated urea containing solution into the granulation section. The term "downstream" generally refers to flowing direction of the respective liquids, vapors or gases. The scrubbing section, preferably the dust scrubbing section, produces an aqueous urea solution of around 30 wt. % to 60 wt. % urea. This aqueous urea solution can be transferred to the second evaporation section different from the before mentioned first evaporation section. As mentioned before, the resulting concentrated urea solution (preferably more than 95 wt. % urea) from the second evaporation section is transferred into the granulation zone. This two section setup (first and second evaporation section) avoids an enrichment or contamination of the first evaporation section. Furthermore by utilizing an acid scrubber in the scrubbing section, the second evaporation section allows a defined introduction of ammonia sulfate [$(NH_4)_2SO_4$] or ammonia nitrate [$NH_4NO_3$] from the scrubbing section via the second evaporation section into the granulation section and the final granular product.

A second condensation section is connected with the second evaporation section. The resulting vapor phase of the second evaporation section is transferred to a second condensation section, different from the first condensation section. The vapor phase is (at least partly) transferred into a preferably mainly liquid phase.

A quenching section comprising a liquid inlet for the distribution or release of a quenching liquid, is (the quenching section) located between and connected to (both) the granulation section and the scrubbing section. The term "liquid inlet" refers to suitable devices for the introduction of liquids into the connection, e.g. pipes or ducts, between the granulation section and the scrubbing section. These devices include nozzles and similar devices. The before mentioned liquid inlet/devices introduce a liquid phase into the gas stream between granulation section and the scrubbing section. Preferably, the liquid inlet introduces the liquid phase in the form of fine dispersed small droplets. The small droplet forming can be achieved by spraying the liquid phase into the before mentioned gas stream. The fine liquid droplets act as a quenching liquid, conditioning the gas stream, lowering the temperature (preferably below 50° C.), e.g. by the phase transition from the liquid to the gas state, and preferably increasing the relative humidity to approximately 100%. A detailed description of the quenching process can be found e.g. in WO 2015/072854 A1, pages 12 to 14. The quenching section is connected with a quenching liquid providing section and the second condensation section. Thereby, the condensate obtained in the second condensation section can be reused in the quenching of the granulator off-gas. In addition, the quenching section is connected with the quenching liquid providing section. The quenching liquid providing section comprises different aqueous liquid sources and related connections for process water, process aqueous liquids or fresh water. Preferably the quenching liquid providing section acts as a source for necessary additional amounts of the quenching liquid. Preferably, the quenching liquid providing section can be a part of the connection (devices) between the granulation section and the scrubbing section or form a separate section between the before mentioned sections.

Preferably the liquid inlet comprises spraying nozzles or similar devices.

In a further preferred embodiment, the scrubbing section comprises a dust scrubber, an acid scrubber and/or a cooler scrubber. Preferably, the dust scrubber utilizes an aqueous urea solution as washing solution. Suitably acid scrubber solutions include sulfuric acid, nitric acid and/or phosphoric acid. Preferably, in the case that an additional granulation cooler is present, this granulation cooler is connected to a separate cooler scrubber. Preferably, this granulation cooler utilizes both a dust and acid scrubber.

Preferably, the dust scrubber is connected with a dust scrubbing liquid providing section. As described above, the term "connected" generally refers to connection means which are able/suitable to transport or transfer process liquids or gases, e.g. pipes, ducts, pumps, hoses. The term "dust scrubbing liquid providing section" includes tanks, reservoirs and/or pumps, suitable for the transport and storage of liquids, respective a suitable dust scrubbing liquids, e.g. water, dilute aqueous urea solutions, dilute or liquid acids.

More preferably, the quenching liquid providing section comprises (is identical with) the dust scrubbing liquid providing section. Both the dust scrubber and the quenching section are connected with the quenching liquid providing section. Thereby the dust scrubbing liquid providing section simultaneously provides the quenching liquid for the quenching section and the dust scrubbing liquid for the dust scrubber. Therefore the same process liquid can be used in two different process steps, reducing the overall process complexity and process costs.

Preferably, the dust scrubber has no freshwater supply. The term "fresh water supply" preferably refers to tap water and/or process water without a significant, process altering amount of impurities. Therefore the dust scrubber does not need an external fresh water support, significantly lowering the process cost and the overall water consumption. A freshwater free supply can be realized, e.g. by connecting the dust scrubbing liquid providing section with the cooler scrubber. As described above, this connection may include pipes, ducts, hoses tanks, reservoirs and/or pumps. More preferably, a scrubbing liquid drainage of the cooler scrubber is connected to a scrubbing liquid inlet of the dust scrubber, thereby transferring the used cooler scrubber liquid into the dust scrubber. This before mentioned connection between the cooler scrubber and the dust scrubber renders an additional fresh water support for the dust scrubber obsolete. Alternatively the freshwater water free supply can be realized in a similar way by a connection between the dust scrubbing liquid providing section and the acid scrubber.

Preferably, a post processing section is connected with the granulation section. This post processing section comprises well known elements like e.g. sieves, crushers, flowing belts, product coolers and elements necessary for the further processing, handling and packaging of the fertilizer granules.

The invention further comprises the use of an inventive urea plant as previously disclosed for the production of fertilizer granules containing ammonia compounds, nitrates, phosphates, urea, elemental sulfur, ammonia sulfate, UAS (urea—ammonia sulfate), and/or mixtures thereof.

Another aspect of the invention relates to a process for the preparation of urea granules at least comprising the following steps.

Carbon dioxide ($CO_2$) is reacted in one or more synthesis and recovery steps with ammonia ($NH_3$) to form a solution (A) comprising urea and water. The principle synthesis and recovery steps are well known in the art, e.g. described in "Ullmann's Encyclopedia of Industrial Chemistry, 2010, Urea, chapter 4, [DOI: 10.1002/14356007.a27_333.pub2]". Preferably the resulting urea solution typically comprises around 50 wt. % to 80 wt. % of urea. A subsequent concentration step is necessary in order to achieve a urea solution with a water content typically below 5 wt. %. This concentration step is achieved by an evaporation of water from solution (A) resulting in a first concentrated urea solution (B) and a first water containing vapor (C). Afterwards, the first water containing vapor (C) is subjected to a condensing step resulting in a first condensate (I). The concentrated urea solution (B) is subjected to a granulation step in a granulation device, resulting in urea granules (D) and a urea dust containing off gas stream (E). The granulation step comprises fluid-bed granulation, prilling or drum granulation, preferably fluid-bed granulation. The urea dust containing off gas stream (E) is subjected to a scrubbing step resulting in an aqueous urea solution (F), e.g. via dust scrubbing. Preferably, the scrubbing step comprises a dust scrubbing, more preferably one or more additional acid scrubbing steps. The aqueous urea solution (F) is subjected to a separate evaporation step resulting in a second concentrated urea solution (G) and a second water containing vapor (H). The second concentrated urea solution (G) is conveyed to the granulation device and reintroduced in the granulation step. The second water containing vapor (H) is subjected to a separate condensation step resulting in a second condensate (J). The second condensate (J) and a quenching liquid (K) are contacted, e.g. in the form of small droplets, with the urea dust containing off-gas stream. Preferably the quenching takes place in a quenching zone, more preferably in the quenching zone described above. The term "off-gas stream" refers to the gas stream leaving the granulation device in the granulation step and before entering the dust scrubbing step.

Preferably, the scrubbing step comprises a dust scrubbing step and/or an acid scrubbing step and/or a cooler scrubbing step.

Preferably, the dust scrubbing step utilizes a dust scrubbing liquid (L) and the dust scrubbing liquid (L) is also used as the quenching liquid (K). This process setup can be realized by connecting the dust scrubber and the quenching section with the same quenching liquid providing section. Thereby the dust scrubbing liquid providing section simultaneously provides the quenching liquid for the quenching section and the dust scrubbing liquid for the dust scrubber. Therefore the same process liquid can used in two different process steps, reducing the overall process complexity and process costs.

According to a preferred embodiment of the invention, the dust scrubbing step utilizes no additional fresh water. This process setup can be realized e.g. by connecting the dust scrubbing liquid providing section with the cooler scrubber. As described above, this connection may include tanks, reservoirs and/or pumps. More preferably, a scrubbing liquid drainage of the cooler scrubber is connected to a scrubbing liquid inlet of the dust scrubber, thereby transferring the used cooler scrubber liquid into the dust scrubber. This before mentioned connection between the cooler scrubber and the dust scrubber renders an additional fresh water support for the dust scrubber obsolete.

FIG. 1 shows the plant setup/process for the preparation of urea granules. The urea production plant comprises at least a synthesis and recovery section (1). In this section ammonia and urea are reacted to form urea. The resulting urea solution comprises typically around 50 wt. % to 80 wt. % of urea. A subsequent concentration step is necessary in order to achieve a urea solution with a water content typically below 5 wt. %. Therefore a first evaporation section (2) is connected with the synthesis and recovery section (1) and a first condensation section (6). The first evaporation section leads to a concentrated urea solution, preferably between 95 wt. % and 98 wt. % of urea and an aqueous vapor stream. The concentrated urea solution is transferred to a granulation section (3) connected with the first evaporation section (2). The granulation section (3) comprises a fluid-bed granulation section. A scrubbing section (4) is connected with the granulation section (3). The cooling air and off-gases from the granulation section are transferred to the scrubbing section (4). Dust, e.g. urea dust, and chemical vapors like ammonia, which are created or released during the granulation process, are removed in the scrubbing unit (4). Optionally, the scrubbing unit comprises at least a dust removing scrubber and an ammonia removing scrubber. A second evaporation section (5) downstream of the scrubbing section is connected with the granulation section (3). The term "downstream" generally refers to flowing direction of the respective liquids, vapors or gases. The scrubbing section (4), in particular the dust scrubbing section, produces an aqueous urea solution of around 30 wt. % to 60 wt. % urea. This aqueous urea solution is transferred to the second evaporation (5) section different from the before mentioned first evaporation section (2). A second condensation section (7) is connected with the second evaporation section (5). The resulting vapor phase of the second evaporation section (5) is transferred to the second condensation section (7), different from the first condensation section (6). The condensed liquid obtained in the second condensation section (7) is reused in the scrubbing unit (4), indicated by the connection between the second condensation section (7) and the scrubbing unit, e.g. as dust scrubbing liquid component. The granulated product of the granulation section (3) is further processed in the post processing section (9). This post processing section (9) comprises well known elements like e.g. sieves, crushers, flowing belts, coolers, elements necessary for the further processing and handling of the granules.

Figure 2:
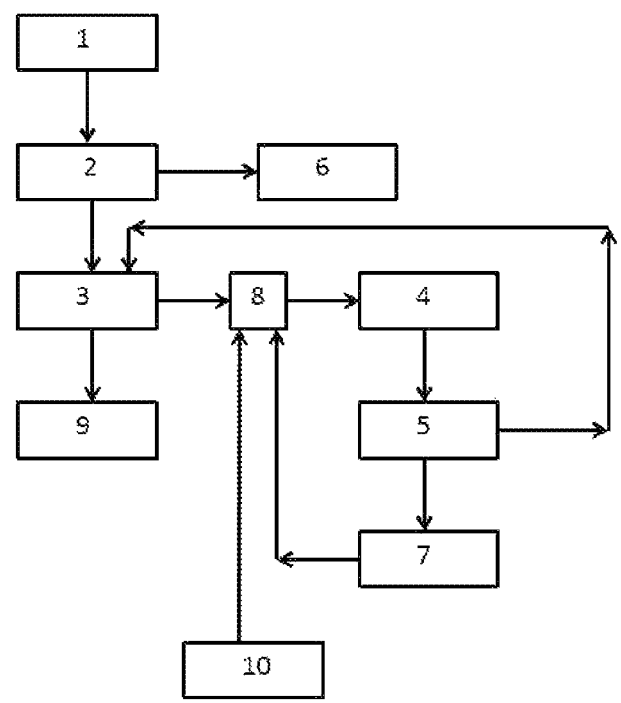
FIG. 2 is a schematic flow diagram of a plant setup/process for the preparation of urea granules.

FIG. 2 shows the schematic flow diagram of a plant setup/process for the preparation of urea granules according to the invention. The basic setup indicated by the reference signs synthesis and recovery section (1), first evaporation section (2), granulation section (3), scrubbing section (4), second evaporation section (5), first condensation section (6), second condensation section (7) and post processing section (9) is identical with the setup described in FIG. 1. However, the second condensation section (7) is connected with a quenching section (8). The quenching section (8) comprising a liquid inlet for the distribution of a quenching liquid is located and connected between the granulation section (3) and the scrubbing section (4). The quenching section (8) is connected with a quenching liquid providing section (10) and the before mentioned second condensation section (7). Thereby, the condensate obtained in the second condensation section can be reused in the quenching of the granulator off-gas. In addition, the quenching section (8) is connected with the quenching liquid providing section (10). The quenching liquid providing section (10) comprises different aqueous liquid sources and related connections for process water, process aqueous liquids or fresh water.

Figure 3:
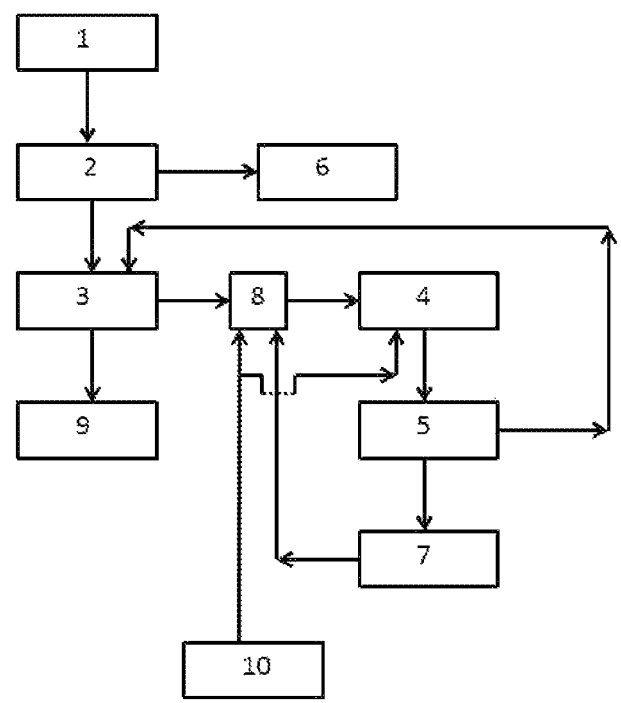
FIG. 3 is a preferred schematic flow diagram of a plant setup/process for the preparation of urea granules.

FIG. 3 shows a preferred schematic flow diagram of a plant setup/process for the preparation of urea granules according to the invention. The principle setup is identical with the setup shown in FIG. 2. In addition, the quenching liquid providing section (10) is connected with the quenching section (8) and the scrubbing section (4), preferably with the dust scrubber. Thereby, the same liquid stream can be used as quenching liquid in the quenching section (8) and as dust scrubbing liquid in the scrubbing section (4). This setup simplifies the overall setup, thereby reducing process costs.

REFERENCE SIGNS (1) synthesis and recovery section
(2) first evaporation section
(3) granulation section
(4) scrubbing section
(5) second evaporation section
(6) first condensation section
(7) second condensation section
(8) quenching section
(9) post processing section
(10) quenching liquid providing section

What is claimed is:

1. A urea production plant, comprising:
a synthesis and recovery section;
a first evaporation section connected to the synthesis and recovery section and a first condensation section;
a granulation section connected to the first evaporation section;
a quenching section comprising a liquid inlet for the distribution of a quenching liquid which is located between and connected to the granulation section and a scrubbing section, wherein the scrubbing section and the granulation section are connected via the quenching section;
a second evaporation section connected to the scrubbing section and connected to the granulation section;
a second condensation section connected to the second evaporation section; and
the quenching section connected to a quenching liquid providing section and the second condensation section.

2. The urea production plant of claim 1 wherein the liquid inlet comprises spraying nozzles.

3. The urea production plant of claim 1 wherein the scrubbing section comprises one or more of a dust scrubber, an acid scrubber, or a cooler scrubber.

4. The urea production plant of claim 3 wherein the dust scrubber is connected with a dust scrubbing liquid providing section.

5. The urea production plant of claim 4 wherein the quenching liquid providing section comprises or is identical to the dust scrubbing liquid providing section and both the dust scrubber and the quenching section are connected to the quenching liquid providing section.

6. The urea production plant of claim 5 wherein the dust scrubber is free of a freshwater supply.

7. The urea production plant of claim 1 wherein a post processing section is connected to the granulation section.

8. A method for the preparation of urea granules, comprising:
one or more synthesis and recovery steps wherein carbon dioxide is reacted with ammonia to form a solution comprising urea and water;
evaporation of water from the solution resulting in a first concentrated urea solution and a first water containing vapor;
subjecting the first water containing vapor to a condensing step resulting in a first condensate;
subjecting the concentrated urea solution to a granulation step resulting in urea granules and a urea dust containing off gas stream;
subjecting the urea dust containing off gas stream to a scrubbing step resulting in an aqueous urea solution;
subjecting the aqueous urea solution to a separate evaporation step resulting in a second concentrated urea solution and a second water containing vapor;
conveying the second concentrated urea solution to the granulation step;
subjecting the second water containing vapor to a separate condensation step resulting in a second condensate; and
subjecting the second condensate and a quenching liquid to the urea dust containing off gas stream after leaving the granulation step and before entering the dust scrubbing step.

9. The method of claim 8 wherein the scrubbing step comprises one or more of a dust scrubbing step, an acid scrubbing step, or a cooler scrubbing step.

10. The method of claim 8 wherein the dust scrubbing step utilizes a dust scrubbing liquid.

11. The method of claim 8 wherein the dust scrubbing step utilizes no additional fresh water.

* * * * *